(12) United States Patent
Bertlein et al.

(10) Patent No.: US 7,776,109 B2
(45) Date of Patent: Aug. 17, 2010

(54) METHOD FOR PRODUCING ACYLPHOSPHINE OXIDE SOLIDS

(75) Inventors: Gerhard Bertlein, Neckargemuend (DE); Karl Heinz Schall, Roemerberg (DE); Matthias Maase, Speyer (DE); Joerg Heilek, Bammental (DE); Dieter Baumann, Frankenthal (DE); Hermann Ascherl, Dirmstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 926 days.

(21) Appl. No.: 10/551,994

(22) PCT Filed: Mar. 30, 2004

(86) PCT No.: PCT/EP2004/003349

§ 371 (c)(1),
(2), (4) Date: Oct. 24, 2006

(87) PCT Pub. No.: WO2004/087723

PCT Pub. Date: Oct. 14, 2004

(65) Prior Publication Data

US 2007/0167653 A1 Jul. 19, 2007

(30) Foreign Application Priority Data

Apr. 4, 2003 (DE) ................. 103 15 671

(51) Int. Cl.
*B01J 6/00* (2006.01)

(52) U.S. Cl. .................................... 23/308 R; 514/183
(58) Field of Classification Search ............. 23/308 R; 514/183

See application file for complete search history.

(56) References Cited

U.S. PATENT DOCUMENTS 5,942,290 A * 8/1999 Leppard et al. ............. 427/510

FOREIGN PATENT DOCUMENTS

| DE | 29 09 994 | 10/1980 |
|---|---|---|
| DE | 30 20 092 | 12/1981 |
| DE | 31 39 984 | 4/1983 |
| EP | 0 007 508 | 2/1980 |
| EP | 0 073 413 | 3/1983 |
| EP | 0 184 095 | 6/1986 |

OTHER PUBLICATIONS

Heinz G. G. O Becker et al., "Organikum-Organisch-chemisches Grundpraktikum" Veb Deutscher Verlag der Wissenschaften, pp. 34-35, 1986.

* cited by examiner

*Primary Examiner*—Edward M Johnson
(74) *Attorney, Agent, or Firm*—Oblon, Spivak, McClelland, Maier & Neustadt, L.L.P.

(57) ABSTRACT

The present invention relates to a process for the preparation of solid acylphosphine oxides by converting an acylphosphine oxide which is in the form of a melt or in dispersed form into the solid state of aggregation with mechanical stress, shearing/internal agitation of the melt.

16 Claims, No Drawings

METHOD FOR PRODUCING ACYLPHOSPHINE OXIDE SOLIDS

The present invention relates to a process for the preparation of solid acylphosphine oxides in which an acylphosphine oxide present as a melt in a continuous phase or in dispersed form is converted to the solid state of aggregation using mechanical stress, shearing/internal agitation of the melt.

The preparation of solid acylphosphine oxides is known, for example, from EP-B1 7 508 (p. 5, l. 19; p. 11, l. 4 ff), DE-A1 30 20 092 (p. 10, l. 29; p. 11, l. 26 ff; p. 12, l. 29 ff), DE-A1 31 39 984 (p. 10, l. 16-25), EP-A2 73 413 (p. 10, Example 1), DE-A 1 29 09 994, p. 14, l. 28-32 or EP-A2 184 095, p. 9, l. 4-6 and l. 14-17.

According to these, acylphosphine oxides with final purity and in the form of a disperse solid are obtained by crystallizing them from the reaction mixture or a solution, i.e. present in molecular disperse form, where appropriate by precipitation. The solvent present in the crystallization solution, i.e. organic solvents or mixtures thereof, may already have been present in the reaction, or it is added as solvent in the work-up, in particular in a recrystallization.

Disadvantages of a crystallization from a solution are:

Need for a solvent which, after crystallization, must either be discarded or else be worked-up before reuse (solvent costs)

Expenditure for separating the crystals off from the residual solution following crystallization (e.g. using filters or centrifuges)

Costly drying of the crystals to which some of the residual solution remains adhered as residual moisture after they have been separated off A reduced yield of acylphosphine oxide since some of the acylphosphine oxide remains in dissolved form in the residual solution which remains following crystallization. Recovery of this part is in most cases difficult and costly, and can usually not be carried out without loss In the case of the use of organic solvents, a high processing expenditure for safe handling of the usually flammable solvents and to avoid emissions It is an object of the present invention to provide a process for acylphosphine oxides which produces solids in a simple and cost-effective manner.

We have found that this object is achieved by a process for the preparation of acylphosphine oxide solids with melting points above room temperature in which the acylphosphine oxide present following reaction or work-up as a continuous melt phase or disperse melt phase into the solid state of aggregation with externally exerted mechanical stress, shearing and/or internal agitation of the melt.

For the purposes of the present invention, acylphosphine oxides are phosphine oxides which carry at least one acyl group, for example mono-, bis- or trisacylphosphines, preferably mono- or bisacylphosphine oxides and particularly preferably monoacylphosphine oxides.

These may, for example, be those phosphine oxides of the formula (I),

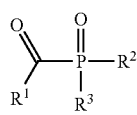

in which $R^1$, $R^2$ and $R^3$, independently of one another, are $C_1$-$C_{18}$-alkyl, $C_2$-$C_{18}$-alkyl optionally interrupted by one or more oxygen and/or sulfur atoms and/or one or more substituted or unsubstituted imino groups, $C_2$-$C_{18}$-alkenyl, $C_6$-$C_{12}$-aryl, $C_5$-$C_{12}$-cycloalkyl or a five- to six-membered heterocycle having oxygen, nitrogen and/or sulfur atoms, where said radicals can each be substituted by aryl, alkyl, aryloxy, alkyloxy, heteroatoms and/or heterocycles, and $R^2$ and $R^3$, independently of one another, may additionally be hydroxy, $C_1$-$C_{18}$-alkoxy optionally substituted by aryl, alkyl, aryloxy, alkyloxy, heteroatoms and/or heterocycles, or $R^1$—(C=O)—.

Here, $C_1$-$C_{18}$-alkyl optionally substituted by aryl, alkyl, aryloxy, alkyloxy, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hepadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di-(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and/or heterocycle-substituted $C_1$-$C_{18}$-alkoxy is, for example, methoxy, ethoxy, n-propyloxy, isopropyloxy, n-butyloxy, isobutyloxy, sec-butyloxy, tert-butyloxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 8-methoxy-1,5-dioxooctyl, 12-methoxy-1,5,9-trioxooctyl, 16-methoxy-1,5,9,13-tetraoxohexadecyl, 8-ethoxy-1,5-dioxooctyl, 12-ethoxy-1,5,9-trioxooctyl, 16-ethoxy-1,5,9,13-tetraoxohexadecyl, 10-hydroxy-1,6-dioxodecyl, 15-hydroxy-1,6,11-trioxopentadecyl, 10-methoxy-1,6-dioxodecyl, 15-methoxy-1,6,11-trioxopentadecyl, 10-ethoxy-1,6-dioxodecyl or 15-ethoxy-1,6,11-trioxopentadecyl, $C_2$-$C_{18}$-alkyl optionally interrupted by one or more oxygen atoms and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5, 10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

The number of oxygen atoms and/or sulfur atoms and/or imino groups is not limited. As a rule, it is not more than 5 in the radical, preferably not more than 4 and very particularly preferably not more than 3.

In addition, at least one, preferably at least two, carbon atoms are usually located between two heteroatoms.

Substituted and unsubstituted imino groups may, for example, be imino, methylimino, isopropylimino, n-butylimino or tert-butylimino.

In addition, $C_6$-$C_{12}$-aryl optionally substituted by aryl, alkyl, aryloxy, alkyloxy, heteroatoms and/or heterocycles is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methyinaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl optionally substituted by aryl, alkyl, aryloxy, alkyloxy, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, and a saturated or unsaturated bicyclic system, such as, for example, norbornyl or norbornenyl, a five- to six-membered heterocycle having oxygen, nitrogen and/or sulfur atoms is, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl and $C_1$ to $C_4$-alkyl is, for example, methyl, ethyl, propyl, isopropyl, n-butyl, sec-butyl or tert-butyl.

The number of substituents in the specified radicals is not limited. As a rule, in the case of radicals with 1 to 3 carbon atoms, it is up to 3 substituents, preferably up to 2 and particularly preferably up to 1. In the case of radicals with 4 to 6 carbon atoms, it is generally up to 4 substituents, preferably up to 3 and particularly preferably up to 1. In the case of radicals with more than 7 carbon atoms, it is generally up to 6 substituents, preferably up to 4 and particularly preferably up to 2.

Preference is given to those acylphosphine oxides as are described in

EP-A2 184 095, particularly from p. 2, l. 4 to p. 5, l. 26 and the examples,

DE-A1 29 09 994, particularly from p. 6, l. 4 to p. 9, l. 14 and the examples,

EP-A2 73 413, particularly from p. 1, l. 27 to p. 3, l. 13 and the examples,

DE-A1 31 39 984, particularly from p. 4, l. 25 to p. 5, l. 20 and the examples,

DE-A 1 30 20 092, p. 5, l. 31 to p. 9, l. 28 and the examples,

EP-B 1 7 508, particularly from p. 1, l. 12 to p. 4, l. 65 and the examples,

DE-C2 42 31 579, particularly p. 2, l. 15 to l. 51 and the examples,

EP-A2 262 629, particularly p. 2, l. 29 to p. 3, l. 54 and the examples,

EP-A2 413 657, particularly p. 1, l. 4 to p. 5, l. 22 and the examples,

EP-B1 942 937, particularly p. 2, l. 1 to p. 5, l. 44 and the examples,

EP-A2 446 175, particularly p. 2, l. 17, p. 5, l. 8 and the examples, and those in the German patent applications with the file reference 10206096.7, 10206117.3 and 10206097.5 and the filing date 13 Feb. 2002.

Within the scope of this disclosure, each of these specifications is hereby expressly incorporated by reference.

Particular preference is given to those acylphosphine oxides in which $R^1$ is chosen from the group consisting of phenyl, 2,6-dimethylphenyl, 2,4,6-trimethylphenyl, 2,6-dimethoxyphenyl or 2,6-dichlorophenyl, $R^2$ is chosen from the group consisting of phenyl, 4-methylphenyl, 2,6-dimethylbenzoyl, 2,4,6-trimethylbenzoyl, 2,6-dimethoxybenzoyl or 2,6-dichlorobenzoyl and $R^3$ is chosen from the group consisting of phenyl, 4-methylphenyl or 2,4,4-trimethyl-pentyl.

Very particular preference is given to 2,4,6-trimethylbenzoyldiphenylphosphine oxide, bis(2,4,6-trimethylbenzoyl)phenylphosphine oxide and bis(2,6-dimethoxybenzoyl)-2,4,4-trimethylpentylphosphine oxide.

In particular, preference is given to 2,4,6-trimethylbenzoyidiphenylphosphine oxide.

The process according to the invention can preferably be used for those acylphosphine oxides whose melting points are above room temperature, i.e. 23° C. The melting point of the acylphosphine oxides which can be used for the process which can be used according to the invention is preferably at least 40° C., particularly preferably at least 50° C. and particularly preferably at least 70° C.

According to the invention, a melt is understood here as meaning a liquid mixture which comprises at least 85% by weight, preferably at least 90% by weight and particularly preferably at least 95% by weight, of the acylphosphine oxide in question. In contrast to this, a solution is a term used according to the invention to mean a molecularly disperse liquid system in which the acylphosphine oxide content is below 85% by weight, or below 90% by weight, or below 95% by weight.

According to the invention, it is also possible for the acylphosphine oxide to be used in disperse form, with the express exclusion of a molecularly disperse distribution, i.e. a solution. According to the invention, in disperse distribution means distributed in liquid form as a melt in another phase, preferably in the form of an emulsion, where the diameter of the droplets is at least 0.1 µm, preferably at least 1 µm and particularly preferably at least 5 µm. However, the acylphosphine oxide is very particularly preferably used as a continuous melt phase.

The other phase which surrounds the acylphosphine oxide droplets may be a liquid or a gas, preferably a liquid, which has low miscibility, or is preferably immiscible, with the acylphosphine oxide. The melt can likewise come into contact, before or during the solidification, with the same type or a different type of solid which is already present.

If a liquid is used as surrounding phase, then this may not be miscible with the acylphosphine oxide in the concentration and temperature range used.

It is preferable if the acylphosphine oxide is soluble in the liquid in an amount less than 10% by weight, preferably in an amount less than 5% by weight, particularly preferably in an amount less than 2% by weight and very particularly preferably in an amount less than 1% by weight.

It is additionally preferable if the liquid is soluble in the acylphosphine oxide in an amount less than 10% by weight, preferably in an amount less than 5% by weight, particularly preferably in an amount less than 2% by weight and very particularly preferably in an amount less than 1% by weight.

In order to find a simple way of producing a solid, attempts were made to convert an acylphosphine oxide melt into a solid directly, i.e. without the use of a solvent and thus avoiding the above disadvantages. In this process, the melt can form directly as a reaction melt, or else be produced from the reaction discharge following suitable work-up steps known per se, such as distillation, rectification, extraction, optionally followed by washing or stripping processes. Such a solidification process is advantageous particularly when no solvent is used in the preceding process stages.

A melt of 2,4,6-trimethylbenzoyldiphenylphosphine oxide (melting point about 92° C.) obtained by reaction of trimethylbenzoyl chloride with ethoxydiphenylphosphine and subsequent multistage extraction, which is left to cool located in a vessel or poured into a dish, becomes increasingly highly viscous as the melt cools, and no or only very sluggish, generally only partial solidification takes place over many hours to several days.

Such a "stationary" cooling without adequate internal agitation of the melt thus does not lead to a practicable/economic solidification step. The known processes such as, for example:

pastilling, i.e. the placing of melt drops onto a cooling surface, for example a steel belt or steel plate, where the drops should usually solidify in the stationary state, in the region of a few minutes, or flaking, i.e. the placing of a melt film onto a cooling surface, for example a steel belt or a roll, where the melt film should convert to a solid layer in the region of a few minutes; said layer can then be removed using a knife by producing fragments, the flakes, are not successful here.

Similarly, a spraying of the melt into a chilled gas to produce droplets which, upon falling through the gas, should solidify to give a disperse solid, is not possible.

It is essential according to the invention that melts or dispersions, preferably melts or emulsions and particularly preferably melts, of acylphosphine oxides can be converted into a solid in short times and without problems if the melt is subjected to mechanical stress during solidification and, as a consequence of this, the melt internally flows, shears or is internally agitated.

According to the invention, mechanical stress is understood as meaning those measures which, in the melt present as a continuous or disperse phase, bring about a convection which goes beyond the natural convection caused by the temperature gradients.

If, for example, a melt is placed onto a cooling plate and the melt is stirred gently by hand (see examples), the formation of a hard solid is achieved in the range of only 1 to 10 min duration (depending on the temperature of the cooling plate).

It has likewise been found that a melt of acylphosphine oxides can be converted without problems into a disperse solid by introducing the melt into a stirred or circulated apparatus (e.g. DTB (Discotherm-B Apparatus) from List, paddle dryer, stirred-tank reactor), and, starting from the continuous melt phase, and processing, with stirring and dissipation of heat, the melt via the suspension state to give a readily flowable solid (discontinuous variant). The solidification is likewise complete here in the region of a few minutes to less than 10 min.

The mechanical stressing of the melt, i.e. the effective force on the melt, causes shearing or internal agitation. Examples of mechanical stress are stirring, pumping, knife coating, scratching, treatment with ultrasound or a stream of gas, for example through a nozzle or an aperture which is passed through the melt or is directed onto its surface.

As a further variant, the melt can be mixed with a solid in an apparatus, for example the melt can be fed onto an initial charge or a solid can be added to the melt, and, following comminution be processed by the mixing/agitation of the solid and melt particles associated with the stirring, from a dispersed melt state to give the disperse solid (continuous or discontinuous procedure).

The initial charge can be created here in the same way or in a different way, i.e. it may be the solid acylphosphine oxide to be purified, or another solid, for example another acylphosphine oxide.

A further embodiment is the continuous or discontinuous introduction of the melt into a solid bed which is not stirred or mixed using mechanical aids, but is mixed/agitated and thereby cooled by means of a stream of fluid. As a rule, a gas is used as fluid, giving rise to a fluidized bed.

The particle size distribution of the solid which arises in the process according to the invention can be controlled by changing the conditions under which the process is carried out and by properties of the apparatus in which the process is carried out. Parameters which can be changed for controlling the particle size here are, for example, type, intensity and duration of the stirring/mixing, manner in which the melt is introduced, for example with or without predistribution, e.g. via nozzles, breaker plates or distributors, presence or type of initial solid charge, for example of a different type or of the same type, operating temperatures, for example up to 90 K below the melting point of the phosphine oxide, type of cooling operation, for example with a cooling rate from 1 to 100 K/h, preferably 5 to 60 K/h and residence time/specific melt throughput of several minutes to a few hours.

Using these parameters, it is possible to produce narrower or broader, and also coarser or finer particle size distributions.

In general, the particle size obtained is smaller the longer and more intensive the energy input or if considerable predistribution takes place, and a broad particle size distribution is obtained if no initial solid charge is used.

As a further variant, the acylphosphine oxide melt can be mixed with a liquid in which the melt is virtually insoluble, giving rise to two liquid phases.

Preferred liquids for this are those which, as stated above, are immiscible and have the stated solubilities of the acylphosphine oxide in the liquid and the stated solubilities of the liquid in the acylphosphine oxide, for example liquids with a $E_T(30)$ value of more than 50, preferably more than 56 and especially preferably ionic liquids ($E_T(30)$ value is a measure of the polarity and is described by C. Reichardt in Reichardt, Christian Solvent Effects in Organic Chemistry Weinheim: VCH, 1979.-XI, (Monographs in Modern Chemistry; 3), ISBN 3-527-25793-4 page 241-242.). The solvents which are listed in Reichardt, loc. cit., on page 242 having an $E_T(30)$ value of more than 50 and especially those having an $E_T(30)$ value of more than 56 are incorporated by reference. By means of intensive agitation, e.g. in a stirred container or a circulation container, the acylphosphine oxide can be converted into a melt state which is present in disperse form and, by dissipating heat, into a disperse solid. Although separating off and drying the solid is then usually necessary, the other specified disadvantages of recovering a solid by solution crystallization are avoided since the losses of product of value via the liquid are minimized.

The processing of the melt to give a disperse solid means that the melt which is present initially usually as a continuous phase is comminuted upon/after introduction into the solidification apparatus (e.g. by emulsification in a liquid or by comminution/mixing into an agitated solid bed), and then, with mechanical stress/internal agitation, triggered by flow forces and/or incidents of impact with particles or internals or walls of the apparatuses, the comminuted melt fractions are solidified as particles on their own and/or as melt films applied to particles already present and/or between particles already present, with the formation of agglomerates.

However, conversion into a disperse solid can also be carried out by, starting from the continuous melt phase, firstly forming solid particles present in dispersed form in this melt (suspension), then, with the continued dissipation of heat, more and more solid particles arise from the melt, so that finally the continuous melt phase converts to a melt phase which is present in disperse form together with the solid, and ultimately is converted completely into a disperse solid. In all of these steps, the formation of new solid from the melt takes place with mechanical stress/internal agitation of the converting melts.

In the case of solidification from the nonstationary, mechanically stressed and thus internally agitated acylphosphine oxide melts, it has been found that inoculation of the solid-free melt with solid which is usually of the same type is not necessary. However, inoculation can accelerate the solidification to a certain degree.

By admixing with a different type of solid, for example 2,4,6-trimethylbenzoyldiphenyl-phosphine oxide with bis(2,4,6-trimethylbenzoyl)phenylphosphine oxide or bis(2,4,6-trimethylbenzoyl)phenylphosphine oxide with bis(2,6-dimethoxybenzoyl)-2,4,4-trimethylpentylphosphine oxide, a formulation of different acylphosphine oxides can be achieved in which the one acylphosphine oxide assists the solidification of the other.

In the case of the nonstationary acylphosphine oxide melt solidification, it has also been found that the temperature of the cooling medium used to dissipate the heat/of the cooling surface used to dissipate the heat has only a moderate influence on the solidification times. Thus, a temperature up to 90 K below the melting point of the phosphine oxide can usually be used, preferably 5 to 70 K, particularly preferably 20 to 60 K. It may, however, be useful to choose the temperature level of the cooling close to the melting point, e.g. 5 to 20 K below the melting point.

The dissipation of heat during the formation of the solid can preferably take place by cooling of apparatus walls. Particularly preferably, the dissipation of heat is effected by indirect cooling via heat exchanger surfaces. Heat transfer means which may be used are all substances and mixtures suitable for this purpose, in particular water, water/methanol or water/glycol mixtures.

In a further embodiment of the invention, it is possible to undertake the dissipation of heat required for the solidification at least in part before and not during the solidification. This may be associated with a supercooling of the melt, i.e. with a cooling below the melting point. However, for correspondingly slower solidification kinetics, such a process can be carried out.

The solid present by solidification according to the invention can be subjected to one or more after-treatments by means of processes known per se in order to change the solid properties as desired. Examples which may be mentioned here are the grinding and/or sieving of the solid to influence the particle size distribution. Solid fractions with undesired properties (e.g. excessively coarse/fine particles) which form during these after treatment steps are returned to the solidification stage preferably in molten form or else in nonmolten form. A feed to another point in the process is, however, also possible.

If the acylphosphine oxide is solidified from an emulsion, further process steps can be undertaken during and/or after the solid-liquid separation to increase the purity of the solid. After the solid has been separated off from the liquid, a single-stage or multi-stage washing may be particularly advantageously carried out. The washing liquid used here is not subject to any limitation, preference being given to water, methanol, ethanol, acetone or mixtures thereof.

The washing can take place in apparatuses customary for this purpose, such as, for example, washing columns, as described, for example, in DE-A 1 100 36 881, in which the removal of the liquid and the washing takes place in an apparatus, in centrifuges, which may be operated in one or more stages, or in suction filters or belt filters. The washing can be carried out on centrifuges or belt filters in one or more stages, the washing liquid preferably being passed countercurrently to the solid.

The mass ratio of washing liquid to solid is usually in the range from 0.1 to 4, particularly preferably in the range from 0.2 to 1 kg of washing liquid per 1 kg of solid.

If the melt to be solidified still comprises fractions of volatile components, the solidification can be carried out under reduced pressure, with at least partial evaporation of these fractions.

The solidification can be carried out in air or under protective gas (inert gas, such as nitrogen, noble gases, $CO_2$ etc.).

The examples below are intended to illustrate the properties of the invention, but without limiting it.

EXAMPLES

Unless stated otherwise, "parts" are understood as meaning "parts by weight".

Comparative Example 1

A melt of 2,4,6-trimethylbenzoyldiphenylphosphine oxide (TPO) (content of TPO: 98.8 area % HPLC) obtained by reaction of trimethylbenzoyl chloride with ethoxydiphenylphosphine (reaction at 80-85° C. in the presence of dimethylcyclohexylamine) and subsequent duplicate extraction (first extraction with basic water/sodium carbonate solution; then with water) was placed, at 95° C., onto a stainless steel cooling plate (cooled with a cooling agent at 30° C.) in the form of a film approximately 3 mm in thickness which then rested on the plate. Even after 7 hours, no conversion to a solid had taken place; the melt remained unchanged in the form of a supercooled highly viscous mass.

Example 1

The same melt as in comparative example 1 was placed at the same application temperature on the plate cooled with cooling medium at 30° C. in the form of a film 3 mm in thickness and then slowly stirred/sheared using a spatula. After about 7 to 8 minutes, a brittle solid was present.

Example 2

The same melt as in comparative example 1 was placed at the same application temperature on the plate cooled with cooling medium at 50° C. in the form of a film 3 mm in thickness and then slowly stirred/sheared using a spatula. After about 2.5 minutes, a brittle solid was present.

Comparative example 2

A melt of 2,4,6-trimethylbenzoyldiphenylphosphine oxide (content of TPO: 99.1 area % HPLC) obtained by reaction of trimethylbenzoyl chloride with ethoxydiphenylphosphine (reaction at 80-85° C. in the presence of dimethylcyclohexylamine) and subsequent 2-fold extraction (first extract with basic water/sodium carbonate solution; then with water) was poured, at 98° C., into a 0.5 l glass flask and cooled therein to room temperature while stationary.

After 4 days, individual needle crystal formations were to be seen only at a few places; the majority of the melt was in the form of a supercooled highly viscous mass.

Example 3

A melt of 2,4,6-trimethylbenzoyldiphenylphosphine oxide (content of TPO: 99.2 area % HPLC) obtained by reaction of trimethylbenzoyl chloride with ethoxydiphenylphosphine (reaction at 80-85° C. in the presence of dimethylcyclohexylamine) and subsequent 2-fold extraction (first extraction with basic water/sodium carbonate solution; then with water) was initially introduced in a first experiment, at 104° C., into a 0.7 l laboratory apparatus of the DTB type in an amount of 0.35 kg. The apparatus was operated at a speed of 30 rpm and cooled using a coolant temperature of 62° C. The melt cooled, became turbid at a temperature of about 80° C. (start of solidification) and then converted within the course of 14 min via the suspension state to a flowable, predominantly finely particulate solid.

Example 4

The same melt as described in example 3 was introduced continuously into a 5 l laboratory apparatus of the paddle dryer type at a mass stream of 3 kg/h, the dryer having already been charged with 1.5 kg of solid prior to starting the introduction of the melt. The apparatus was operated at a speed of 30 rpm and cooled using a coolant temperature of 20° C. The melt was mixed into the solid located in the apparatus by the rotating mixing elements and discharged as a flowable, particulate solid after an average residence time of about 45 min at the end of the apparatus opposite to the melt feed. The temperature of the discharged solid was 25° C.

The particle size distribution for this type of solidification was: 9% by weight >2.8 mm; 50.5% by weight of 0.9 to 2.8 mm; 17.9% by weight from 0.56 to 0.9 mm; remainder <0.56 mm.

Example 5

A melt of 2,4,6-trimethylbenzoyldiphenylphosphine oxide (content of TPO: 95.8 area % HPLC) obtained by reaction of trimethylbenzoyl chloride with ethoxydiphenylphosphine was placed, at 100° C., onto a stainless steel cooling plate (cooled using a coolant at 60° C.) in the form of a melt coating approximately 3.5 mm in thickness and slowly stirred/sheared using a spatula during cooling. After 2 minutes, a hard, crumbly solid was present.

Comparative example 3

A 2,4,6-trimethylbenzoylbis(2,5-dimethylphenyl)phosphine oxide melt with a melting point of 136° C. was placed onto a stainless steel cooling plate in the form of a film approximately 3 mm in thickness in three experiments each at 145° C., on which plate the melt film then rested. The plate was cooled using coolant temperatures of 50, 80 and 110° C. In all three cases no, not even partial, solidification could be observed within 15 minutes. The melt remained as a supercooled, clear and viscous-tacky film on the plate.

Examples 6 and 7

The same melt as in comparative example 3 was placed onto the cooling plate in two further experiments with the same feed temperature (145° C.) again in the form of a film 3 mm in thickness, and then slowly stirred/sheared using a spatula. In both experiments, a hard lumpy solid was present after a short time (in the case of a cooling medium temperature of 80° C. after 4.5 minutes, in the case of a cooling medium temperature of 110° C. after 2.5 minutes).

What is claimed is:

1. A process for the preparation of an acylphosphine oxide solid with a melting point above room temperature, which comprises converting the acylphosphine oxide present following reaction or work-up as a continuous melt phase or disperse melt phase into the solid state of aggregation with externally exerted mechanical stress of the melt during solidification, whereby the melt internally flows, shears or is internally agitated, wherein the acylphosphine oxide is selected from the group consisting of 2,4,6-trimethylbenzoyldiphenylphosphine oxide, bis(2,4,6-trimethylbenzoyl)phenylphosphine oxide and bis(2,6-dimethoxybenzoyl)-2,4,4-trimethylpentylphosphine oxide.

2. A process as claimed in claim 1, wherein the melt is a liquid mixture which comprises the acylphosphine oxide in an amount of at least 85% by weight.

3. A process as claimed in claim 1, wherein a dispersion of the acylphosphine oxide present in dispersed form is distributed as droplets with a diameter of at least 0.1 μm in another phase.

4. A process as claimed in claim 1, wherein the mechanical stress of the melt is caused by stirring, pumping, knife coating, scratching, treatment with ultrasound or a stream of gas, which is passed through the melt or directed onto its surface.

5. A process as claimed in claim 1, wherein the melt is mixed with a solid.

6. A process as claimed in claim 1, wherein the melt is mixed with a liquid in which the melt is soluble in an amount of not more than 10% by weight.

7. A process as claimed in claim 6, wherein the melt is mixed with a liquid which is soluble in the acylphosphine oxide in an amount of not more than 10% by weight.

8. A process as claimed in claim 6, wherein the liquid is an ionic liquid.

9. A process as claimed in claim 1, wherein the acylphosphine oxide is 2,4,6-trimethyl-benzoyldiphenyl-phosphine oxide.

10. A process as claimed in claim 7, wherein the liquid is an ionic liquid.

11. A process as claimed in claim 6, wherein the liquid has an $E_T(30)$ value of more than 50.

12. A process as claimed in claim 6, wherein the liquid has an $E_T(30)$ value of more than 56.

13. A process as claimed in claim 7, wherein the liquid has an $E_T(30)$ value of more than 50.

14. A process as claimed in claim 7, wherein the liquid has an $E_T(30)$ value of more than 56.

15. A process as claimed in claim 2, wherein the mechanical stress of the melt is caused by stirring, pumping, knife coating, scratching, treatment with ultrasound or a stream of gas, which is passed through the melt or directed onto its surface.

16. A process as claimed in claim 3, wherein the mechanical stress of the melt is caused by stirring, pumping, knife coating, scratching, treatment with ultrasound or a stream of gas, which is passed through the melt or directed onto its surface.

* * * * *